United States Patent
Schmidt et al.

(10) Patent No.: US 11,485,703 B2
(45) Date of Patent: Nov. 1, 2022

(54) PROCESS FOR MANUFACTURING A COMPLEXING AGENT

(71) Applicant: BASF SE, Ludwigshafen am Rhein (DE)

(72) Inventors: Thomas Schmidt, Ludwigshafen (DE); Armin Stamm, Ludwigshafen (DE); Marta Reinoso Garcia, Ludwigshafen (DE); Verena Mormul, Ludwigshafen (DE); Michael Klemens Mueller, Ludwigshafen (DE); Frank Jaekel, Ludwigshafen (DE); Jeremy T Manning, Wyandotte, MI (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/626,026

(22) PCT Filed: Jun. 19, 2018

(86) PCT No.: PCT/EP2018/066239
§ 371 (c)(1),
(2) Date: Dec. 23, 2019

(87) PCT Pub. No.: WO2019/002022
PCT Pub. Date: Jan. 3, 2019

(65) Prior Publication Data
US 2021/0094902 A1    Apr. 1, 2021

(30) Foreign Application Priority Data
Jun. 28, 2017   (EP) ..................................... 17178447

(51) Int. Cl.
*C07C 227/26* (2006.01)
*C07C 229/16* (2006.01)

(52) U.S. Cl.
CPC .......... *C07C 227/26* (2013.01); *C07C 229/16* (2013.01)

(58) Field of Classification Search
None
See application file for complete search history.

(56) References Cited

U.S. PATENT DOCUMENTS

| | | | |
|---|---|---|---|
| 5,543,566 A * | 8/1996 | Takahashi | C07C 227/26 562/571 |
| 7,671,234 B2 | 3/2010 | Oftring et al. | |
| 7,754,911 B2 | 7/2010 | Oftring et al. | |
| 2008/0194873 A1 * | 8/2008 | Oftring | C07C 227/26 562/571 |
| 2012/0071381 A1 | 3/2012 | Mrzena et al. | |
| 2018/0105486 A1 | 4/2018 | Stamm et al. | |

FOREIGN PATENT DOCUMENTS

| | | |
|---|---|---|
| CN | 101171226 A | 4/2008 |
| CN | 105531255 A | 4/2016 |
| WO | WO 2010/133617 A1 | 11/2010 |
| WO | 2012/150155 A1 | 11/2012 |
| WO | WO 2016/180664 A1 | 11/2016 |
| WO | WO 2018/197249 A1 | 11/2018 |

OTHER PUBLICATIONS

Extended European Search Report dated Jan. 3, 2018 in Patent Application No. 17178447.3, 3 pages.
International Preliminary Report on Patentability dated Jun. 18, 2019 in PCT/EP2018/066239 filed Jun. 19, 2018, 6 pages.
Written Opinion of the International Searching Authority dated Sep. 6, 2018 in PCT/EP2018/066239 filed Jun. 19, 2018, therein, 6 pages.
U.S. Appl. No. 16/607,259, filed Oct. 22, 2019, Marta Reinoso Garcia, et al.
International Search Report dated Sep. 6, 2018 in PCT/EP2018/066239 filed on Jun. 19, 2018.

* cited by examiner

*Primary Examiner* — Amy C Bonaparte
(74) *Attorney, Agent, or Firm* — ArentFox Schiff LLP

(57) ABSTRACT

The present invention is directed towards a process for manufacturing a complexing agent, said process comprising the steps of (a) Providing a nitrile according to general formula (I a) or (I b)

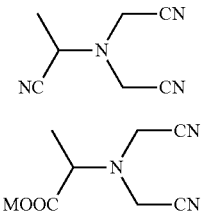

With M being selected from alkali metal and hydrogen and combinations thereof, (b) Saponification with a total alkali amount of 2.5 to 2.9 mol of alkali metal hydroxide per mole of nitrile according to general formula (I a) or (I b), respectively, and a pH value in the range of from 9.5 to 11.5 at the end of step (b), (c) Adding an amount of alkali metal hydroxide so that the total alkali content is 2.9 to 3.15 moles per mole nitrile according to general formula (I a) or (I b), respectively, and (d) Allowing further conversion.

9 Claims, No Drawings

PROCESS FOR MANUFACTURING A COMPLEXING AGENT

The present invention is directed towards a process for manufacturing a complexing agent, said process comprising the steps of
(a) Providing a nitrile according to general formula (I a) or (I b)

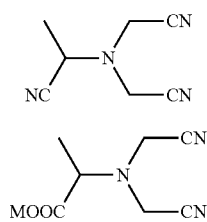

With M being selected from alkali metal and hydrogen and combinations thereof,
(b) Saponification with a total alkali amount of 2.5 to 2.9 mol of alkali metal hydroxide per mole of nitrile according to general formula (I a) or (I b), respectively, and a pH value in the range of from 9.5 to 11.5 at the end of step (b),
(c) Adding an amount of alkali metal hydroxide so that the total alkali content is 2.9 to 3.15 moles per mole nitrile according to general formula (I a) or (I b), respectively, wherein, if a total of 2.9 moles alkali metal hydroxide per mole of nitrile are employed the amount of alkali in the respective step (b) is in the range of from 2.5 to less than 2.9 moles, and
(d) Allowing further conversion.

Chelating agents such as, but not limited to methyl glycine diacetic acid (MGDA) and their respective alkali metal salts are useful sequestrants (chelating agents) for alkaline earth metal ions such as $Ca^{2+}$ and $Mg^{2+}$ and of transition metals such as, but not limited to $Fe(+II)/Fe(+III)$. For that reason, they are recommended and used for various purposes such as laundry detergents and for automatic dishwashing (ADW) formulations, in particular for so-called phosphate-free laundry detergents and phosphate-free ADW formulations.

MGDA and other chelating agents may be made by an alkylation of amino acids with formaldehyde and hydrocyanic acid or an alkali metal cyanide followed by saponification with alkali metal hydroxide. In order to secure complete saponification a stoichiometric amount of alkali metal hydroxide or an excess of alkali metal hydroxide is applied, see, e. g., U.S. Pat. No. 7,671,234. In other methods, MGDA is made by addition of $NH(CH_2CN)_2$ and hydrocyanic acid to acetaldehyde under formation of a trinitrile, followed by hydrolysis, see, e.g., U.S. Pat. No. 7,754,911.

In order to reduce reduced corrosion issues if the saponification is performed in reactors from stainless steels such as 316 steel, it has been proposed in WO 2016/180664 to use a sub-stoichiometric amount of base. Mixtures from MGDA and monoamides are obtained that exhibit a good complexing behaviour. However, under certain conditions solidification by methods like spray drying or spray granulation is economically unfavourable because a comparably high share of too large particles ("overs") is created. Although it is possible to remove such overs and mill them down before recycling them such a share of overs is undesirable for economical and process performance reasons.

It was thus an objective to provide a complexing agent with excellent long-term colour stability that may be solidified easily and under economic conditions.

Accordingly, the process defined at the outset was found, hereinafter also referred to as inventive process. The inventive process comprises the steps of
(a) Providing a nitrile according to general formula (I a) or (I b)

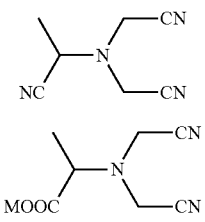

With M being selected from alkali metal and hydrogen and combinations thereof,
(b) Saponification with a total alkali amount of 2.5 to 2.9 mol of alkali metal hydroxide per mole of nitrile according to general formula (I a) or (I b), respectively, and a pH value in the range of from 9.5 to 11.5 at the end of step (b),
(c) Adding an amount of alkali metal hydroxide so that the total alkali content is 2.9 to 3.15 moles per mole nitrile according to general formula (I a) or (I b), respectively, wherein, if a total of 2.9 moles alkali metal hydroxide per mole of nitrile are employed the amount of alkali in the respective step (b) is in the range of from 2.5 to less than 2.9 moles, and
(d) Allowing further conversion.

Said steps are hereinafter also referred to as step (a), step (b), step (c) and step (d). They are described in more detail below.

Nitriles according to general formulae (I a) and (I b) are known per se. Nitrile (I a) may be made by reacting $NH(CH_2CN)_2$ and hydrocyanic acid with acetaldehyde. Nitrile (I a) is usually racemic.

Nitrile (I b) is advantageously made by conversion of alanine in a so-called double Strecker synthesis with two equivalents of HCN and formaldehyde each. Nitrile (I b) may be racemic or the L-isomer or any mixture of L- and D-isomers with predominantly the L-isomer, for example with 50 to 99.5% L-enantiomer. Preferred are the racemic mixtures and mixtures that contain 95 to 99.5% L-enantiomer. Nitrile (I b) may be provided as free acid or fully or partially neutralized with alkali, for example with sodium or potassium.

In step (a), nitrile according to general formulae (I a) and (I b) may be provided in bulk or as solution or slurry, for example in a concentration—or solids content—in the range of from 5 to 60% by weight.

Said slurry or solution is preferably an aqueous slurry or an aqueous solution, preferably an aqueous solution. Such slurry or solution, respectively, may have a total solids content in the range of from 5 to 60% by weight, preferably 30 to 50% by weight. The term "aqueous" refers to a continuous phase or solvent comprising in the range of from 50 to 100 vol-% of water, preferably 70 to 100 vol-% of water, referring to the total continuous phase or solvent, respectively. Examples of suitable solvents other than water are alcohols such as methanol, ethanol and isopropanol, furthermore diols such as ethylene glycol and triols such as glycerol.

In step (b), nitrile according to general formula (I a) or (I b), respectively, is saponified with a total alkali amount of 2.5 to 2.9 mole alkali metal hydroxide per mole of nitrile according to general formula (I a) or (I b), respectively, and a pH value of from 9.5 to 11.5 at the end of step (b). The pH value is determined at ambient temperature and refers to the pH value at the end of the saponification according to step (b) as is without further dilution. Immediately after the addition of said alkali metal hydroxide in step (b), the pH value is higher than 11.5, for example up to 14. In the course of consumption of alkali metal hydroxide the pH value decreases.

In one embodiment of the present invention alkali metal hydroxide is selected from hydroxides of lithium, sodium, potassium and combinations of least two of the foregoing. Preferred are sodium hydroxide, potassium hydroxide, mixtures of sodium hydroxide and potassium hydroxide and even more preferred is sodium hydroxide.

In step (b), alkali metal hydroxide may be added to nitrile according to general formula (I a) or (I b), respectively, in bulk or preferably in aqueous solution. Aqueous solutions of alkali metal hydroxide may have a concentration in the range of from 1% by weight to 65% by weight, preferably from 10 to 55% by weight.

Aqueous solutions of alkali metal hydroxide may contain one or more impurities such as, but not limited to alkali metal carbonate. For example, aqueous solutions of sodium hydroxide may contain 0.01 to 1% sodium carbonate.

Step (b) may be started by charging a reaction vessel with an aqueous solution of alkali metal hydroxide and then adding slurry or solution of compound according to general formula (I a) or (I b), respectively, in one or more portions. In an alternative embodiment, said contacting may be performed by charging a reaction vessel with a portion of aqueous solution of alkali metal hydroxide and then adding slurry or solution of compound according to general formula (I a) or (I b), respectively, in one or more portions, and the remaining solution of alkali metal hydroxide, consecutively or preferably in parallel. In an alternative embodiment, said contacting may be performed by continuously combining solution or slurry of compound according to general formula (I a) or (I b) and aqueous solution of alkali metal hydroxide.

In embodiments in which aqueous solutions of alkali metal hydroxide are added in two portions in step (b), the first portion may contain 10 to 50 mole-% of the required alkali metal hydroxide and the second portion may contain the remaining 50 to 90 mole-%.

In embodiments in which compound according to general formula (I a) or (I b) is added in two portions in step (b), the first portion may contain 10 to 50 mole-% of the required compound according to general formula (I a) or (I b) and the second portion may contain the remaining 50 to 90 mole-%.

In one embodiment of the present invention, the reaction vessel in which step (b) is performed contains at least one part made from stainless steel or stainless steel that is exposed to the mixture formed in step (b). Stainless steel here refers to pure austenitic stainless steels or alloys of austenitic and ferritic stainless steels (e.g. "Duplex steel").

Step (b) is performed with in the range of from 2.5 to 2.9 of alkali metal hydroxide per mole of nitrile according to general formula (I a) or (I b), respectively. In the context of step (b), said amount of alkali metal hydroxide includes alkali metal hydroxide that has been used during the manufacture of nitrile according to general formula (I a) or (I b). At the end of step (b), the pH value is in the range of from 9.5 to 11.5.

Step (b) of the inventive process may be performed at a temperature in the range of from 25 to 200° C., preferably 45 to 190° C.

Step (b) of the inventive process may be performed at one temperature. In preferred embodiments, however, step (b) is performed in the form of two or more sub-steps (b1), (b2) and optionally more, of which the sub-steps are performed at different temperatures. Preferably, each sub-step may be performed at a temperature that is higher than the temperature at which the previous sub-step was performed. In the context of the present invention, sub-steps differ in temperature by at least 10° C., said temperature referring to the average temperature. In a preferred embodiment of the present invention, step (b) comprises at least two sub-steps (b1) and (b2), sub-step (b2) being performed at a temperature at least 20° C. higher than sub-step (b1), preferably at least 25° C. In a preferred embodiment, step (b) comprises at least two sub-steps (b1) and (b2), sub-step (b2) being performed at a temperature from 20° C. to 150° C. higher than sub-step (b1).

Preferably, a sub-step is performed over a period of at least 30 minutes. Even more preferably, a sub-step is performed over a period of 30 minutes to 5 hours, preferably up to 2 hours. In one embodiment of the present invention, step (b) has an overall duration in the range of from 30 minutes up to 24 hours, preferably 2 to 16 hours.

In one embodiment of the present invention, at least one sub-step of step (b) is carried out at a temperature in the range of from 25 to 50° C., preferably at least one in the range of from 40 to 55° C.

In one embodiment of the present invention, at least one sub-step of step (b) is carried out at a temperature in the range of from 50 to 80° C., preferably 60 to 75° C.

In one embodiment of the present invention, at least one sub-step of step (b) is carried out at a temperature in the range of from 90 to 200° C., preferably 150 to 190° C.

In one embodiment of the present invention, at least one sub-step of step (b) is carried out at a temperature in the range of from 25 to 60° C., another sub-step of step (b) is carried out at a temperature in the range of from 50 to 80° C., and at least another sub-step of step (b) is carried out at a temperature in the range of from 100 to 200° C.

In one embodiment of the present invention, ammonia formed during the reaction is removed, continuously or discontinuously, for example by stripping or by distilling it off, for example at a temperature of at least 90° C., preferably 90 to 105° C.

In one embodiment of the present invention, water is added during the course of step (b), for example in order to compensate for the loss of water due to ammonia removal.

In one embodiment of the present invention, step (b) is carried out at normal pressure or at a pressure above 1 bar, for example 1.1 to 40 bar, preferably 5 to 25 bar. In embodiments with two or more sub-steps of step (b), subsequent sub-steps are preferably carried out at a pressure at least as high as the previous sub-step.

Step (b) may be carried out in a stirred tank reactor, or in a plug flow reactor, or in a cascade of at least two stirred tank reactors, for example 2 to 6 stirred tank reactors, or in a combination of a cascade of 2 to 6 stirred tank reactors with at least one plug flow reactor, or in a cascade of at least one stirred tank reactor and two plug flow reactors.

Especially in embodiments wherein the final sub-step of step (b) is carried out in a plug flow reactor, said final sub-step may be carried out at elevated pressure such as 1.5 to 40 bar, preferably at least 20 bar. The elevated pressure may be accomplished with the help of a pump or by autogenic pressure elevation.

In one embodiment of the present invention, the reaction vessel in which step (b) is performed contains at least one part made from stainless steel that is exposed to the reaction mixture according to step (b).

In one embodiment of the present invention, at least one reaction vessel in which a sub-step of step (b) is performed contains at least one part made from stainless steel that is exposed to the reaction mixture according to step (b).

During step (b), a partial or complete racemization may take place if compound according to general formula (I a) or (I b) is optically active and if step (b) or at least one sub-step of step (b) is carried at a sufficiently high temperature. Without wishing to be bound by any theory, it is likely that racemization takes place on the stage of the above L-monoamide or L-diamide or of the L-isomer of MGDA.

After step (b), the solution of the products so obtained is usually allowed to cool down, for example to 70 to 100° C., especially in the range of from 80 to 100° C. In embodiments in which step (b) or at least a sub-step of step (b) is performed under a pressure higher than 1 bar it is preferred to reduce the pressure to normal pressure after step (b).

In step (c), an amount of alkali metal hydroxide is added so that the total alkali content is 2.9 to 3.15 moles per mole nitrile according to general formula (I a) or (I b), respectively. In the context of step (c), said amount of alkali includes alkali metal hydroxide that has been used during the manufacture of nitrile according to general formula (I a) or (I b). Preferred in step (c) are 2.9 to 3.0 moles. In embodiments wherein a total of 2.9 moles alkali metal hydroxide per mole of nitrile are employed the amount of alkali in the respective step (b) is in the range of from 2.5 to less than 2.9 moles, for example 2.85 moles.

For performing step (c), alkali metal hydroxide may be selected from lithium hydroxide, sodium hydroxide and potassium hydroxide and combinations of at least two of the foregoing, for example combinations of sodium hydroxide and potassium hydroxide. Preferred alkali metal hydroxide in step (c) is sodium hydroxide. In a preferred embodiment of the present invention, alkali metal hydroxide in step (b) and alkali metal hydroxide in step (c) are both sodium hydroxide.

The addition of alkali metal hydroxide may be accomplished by adding solid alkali metal hydroxide or by addition of an aqueous solution of alkali metal hydroxide.

In one embodiment of the present invention the addition of alkali metal hydroxide according to step (c) is performed at a temperature in the range of from 20 to 100° C. If the addition is performed at higher temperature, a certain pressure higher than normal pressure needs to be applied which needs extra efforts.

Step (d) of the inventive process includes allowing further conversion. This means that further saponification may occur. In other embodiments, step (d) includes a further neutralization without hydrolysis. Step (d) may include a removal of ammonia as well.

In one embodiment of the present invention, the aqueous solution resulting from step (c) is refluxed at normal pressure, for example over a period of time in the range of from 30 minutes to 5 hours.

The steps (a), (b), (c) and (d) of the inventive process are performed in the order as described above.

In one embodiment of the present invention, the inventive process may comprise additional steps other than steps (a), (b), (c) and (d) disclosed above. Such additional steps may be, for example, one or more decolourization steps, for example treatment with activated carbon or with peroxide such as $H_2O_2$ or by irradiation with UV-light in the absence or presence of $H_2O_2$.

In one embodiment of the present invention ammonia is removed between steps (b) and (d), for example partially or completely.

In one embodiment of the present invention the inventive process comprises an additional step (e) of spray-drying or spray granulating the resultant complexing agent A further step other than step (a), (b), (c) or (d) that may be carried out after step (c) or during step (d) or after step (d) is stripping with air or nitrogen or steam in order to remove ammonia. Said stripping can be carried out at temperatures in the range of from 90 to 110° C. By nitrogen or air stripping, water can be removed from the solution so obtained. Stripping is preferably carried out at a pressure below normal pressure, such as 650 to 950 mbar.

In embodiments wherein a solution is desired, the solution obtained from step (d) is just cooled down and, optionally, concentrated by partially removing the water. If dry samples of inventive mixtures are required, the water can be removed by spray drying or spray granulation.

The inventive process may be carried out as a batch process, or as a semi-continuous or continuous process.

As a result of the inventive process, an aqueous solution of methyl glycine diacetate (MGDA) is obtained with excellent long-term colour stability.

MGDA obtained according to the inventive process may be a racemic mixture or a pure enantiomer, for example the L-enantiomer, or a mixture of L- and D-enantiomers in which one of the enantiomers prevails, preferably the L-enantiomer prevails. In a preferred embodiment of the present invention MGDA obtained according to the inventive process is a mixture of enantiomers containing predominantly the respective L-enantiomer with an enantiomeric excess (ee) in the range of from 10 to 98%.

In one embodiment of the present invention, the enantiomeric excess of the respective L-isomer of MGDA obtained according to the inventive process is in the range of from 10 to 98%, preferably in the range of from 12.5 to 85% and even more preferred up to 75%. In other embodiments, all components of inventive mixtures constitute the respective racemic mixtures.

In embodiments where MGDA obtained according to the inventive process comprises two or more compounds, the ee refers to the enantiomeric excess of all L-isomers present in MGDA obtained according to the inventive process compared to all D-isomers in the respective MGDA. For example, in cases wherein a mixture of the di- and trisodium salt of MGDA is present, the ee refers to the sum of the disodium salt and trisodium salt of L-MGDA with respect to the sum of the disodium salt and the trisodium salt of D-MGDA.

The enantiomeric excess can be determined by measuring the polarization (polarimetry) or preferably by chromatography, for example by HPLC with a chiral column, for example with one or more cyclodextrins as immobilized phase. Preferred is determination of the ee by HPLC with an immobilized optically active ammonium salt such as D-penicillamine.

In one embodiment of the present invention, MGDA obtained according to the inventive process may contain in the range of from 0.1 to 10% by weight of one or more optically inactive impurities, at least one of the impurities being at least one of the impurities being selected from iminodiacetic acid, racemic N-carboxymethylalanine, formic acid, glycolic acid, propionic acid, acetic acid and their respective alkali metal or mono-, di- or triammonium salts.

In one aspect of the present invention, MGDA obtained according to the inventive process may contain less than 0.2% by weight of nitrilotriacetic acid (NTA), preferably 0.01 to 0.1% by weight.

In one embodiment of the present invention, MGDA obtained according to the inventive process may contain one or more optically active impurities. Examples of optically active impurities are L-carboxymethylalanine and its respective mono- or dialkali metal salts, and optically active mono- or diamides that result from an incomplete saponification of the dinitriles, see below. Preferably, the amount of optically active impurities is in the range of from 0.01 to 2% by weight, referring to the inventive mixture solution. Even more preferred, the amount of optically active impurities is in the range of from 0.1 to 2% by weight.

In one aspect of the present invention, MGDA obtained according to the inventive process may contain minor amounts of cations other than alkali metal. It is thus possible that minor amounts, such as 0.01 to 5 mol-% of total inventive mixture, based on anion, bear ammonium cations or alkali earth metal cations such as $Mg^{2+}$ or $Ca^{2+}$, or transition metal ions such as $Fe^{2+}$ or $Fe^{3+}$ cations.

In one embodiment of the present invention, the inventive process comprises the additional step (e) of spray-drying or spray granulating the complexing agent resulting from step (d). by performing step (e), powders or granules may be obtained. In the context of the present invention, powders are particulate materials that are solids at ambient temperature and that preferably have an average particle diameter in the range of from 1 μm to less than 0.1 mm, preferably 5 μm up to 50 μm. The average particle diameter of powders can be determined, e.g., by LASER diffraction methods, for example with Malvern apparatus, and refers to the volume average. In the context of the present invention, granules are particulate materials that are solids at ambient temperature and that preferably have an average particle diameter in the range of from 0.1 mm to 2 mm, preferably 0.4 mm to 1.25 mm. The average particle diameter of granules can be determined, e.g., by optical or preferably by sieving methods. Sieves employed may have a mesh in the range of from 60 to 1,250 μm.

In one embodiment of the present invention, powders or granules have a broad particle diameter distribution. In another embodiment of the present invention, powders or granules have a narrow particle diameter distribution. The particle diameter distribution can be adjusted, if desired, by multiple sieving steps.

Granules and powders may contain residual moisture, moisture referring to water including water of crystallization and adsorbed water. The amount of water may be in the range of from 0.1 to 20% by weight, preferably 1 to 15% by weight, referring to the total solids content of the respective powder or granule, and may be determined by Karl-Fischer-titration or by drying at 160° C. to constant weight or for a dedicated time range, e.g. one hour, with an infrared radiator.

In one especially preferred embodiment of the present invention, the amount of water in powder may be in the range of 5 to 10% by weight.

In one especially preferred embodiment of the present invention, the amount of water in granules may be in the range of 9 to 12% by weight.

Particles of powders may have regular or irregular shape. Preferred shapes of particles of powders are spheroidal shapes.

Particles of granules may have regular or irregular shapes. Preferred shapes of particles of granules are spheroidal shapes.

Spray-drying or spray granulation in accordance with step (e) may be performed using a gas with an inlet temperature of preferably at least 125° C. Said gas, hereinafter also being referred to as "hot gas", may be nitrogen, a rare gas or preferably air. In the course of step (e), most of the water will be removed, for example at least 55%, preferably at least 65% of the water. In one embodiment of the present invention, up to 95% of the water at most will be removed.

Spray-drying and spray granulation will be described in more detail below.

In one embodiment of the present invention, a drying vessel, for example a spray chamber or a spray tower, is being used in which a spray-drying process is performed. A solution or slurry of MGDA obtained according to the inventive process is sprayed into said spray chamber or spray tower together with a hot gas stream in parallel or countercurrent flow. The hot gas stream may have a temperature in the range of from 60 to 350° C., preferably 125 to 220° C.

In one embodiment of the present invention, a drying vessel, for example a spray chamber or a spray tower, is being used in which a spray-granulating process is performed by using a fluidized bed. Such a drying vessel is charged with a fluidized bed of MGDA seed particles, obtained by any drying method such as spray drying or evaporation crystallization. Fluidization of the bed is achieved by a gas stream with a temperature in the range of from 125 to 350° C., preferably of from 125 to 220° C. Then, a solution or slurry of MGDA obtained according to the inventive process is sprayed onto or into such fluidized bed together with a hot gas stream with a temperature in the range of from 60 to 250° C., preferably 125 to 220° C.

In one embodiment of the present invention, the fluidized bed may have a temperature in the range of from 80 to 150° C., preferably from 90 to 120° C.

Spraying is being performed through one or more nozzles per drying vessel. Suitable nozzles are, for example, high-pressure rotary drum atomizers, rotary atomizers, single-fluid nozzles and two-fluid nozzles, two-fluid nozzles and rotary atomizers being preferred. The first fluid is the solution or slurry obtained according to step (d) of the inventive process, the second fluid is compressed gas, for example with a pressure of 1.1 to 7 bar. For spray granulation, preferred nozzles are selected from single-fluid nozzles and two-fluid nozzles. The expressions two-fluid nozzles and two-component nozzles may be used interchangeably.

In one embodiment of the present invention, the droplets formed during the spray-granulating have an average diameter in the range of from 10 to 500 μm, preferably from 20 to 180 μm, even more preferably from 30 to 100 μm.

In one embodiment of the present invention, the off-gas departing the drying vessel may have a temperature in the range of from 40 to 140° C., preferably 80 to 110° C. but in any way colder than the hot gas stream. Preferably, the temperature of the off-gas departing the drying vessel and the temperature of the solid product present in the drying vessel are identical.

In another embodiment of the present invention, spray-granulation is being performed by performing two or more consecutive spray-drying processes, for example in a cascade of at least two spray dryers, for example in a cascade of at least two consecutive spray towers or a combination of a spray tower and a spray chamber, said spray chamber containing a fluidized bed. In the first dryer, a spray-drying process is being performed in the way as follows.

Spray-drying may be preferred in a spray dryer, for example a spray chamber or a spray tower. A solution or slurry obtained according to step (a) with a temperature preferably higher than ambient temperature, for example in the range of from 50 to 95° C., is introduced into the spray dryer through one or more spray nozzles into a hot gas inlet stream, for example nitrogen or air, the solution or slurry being converted into droplets and the water being vaporized. The hot gas inlet stream may have a temperature in the range of from 125 to 350° C.

The second spray dryer is charged with a fluidized bed with solid from the first spray dryer and solution or slurry obtained according to the above step is sprayed onto or into the fluidized bed, together with a hot gas inlet stream. The hot gas inlet stream may have a temperature in the range of from 125 to 350° C., preferably 160 to 220° C.

In one embodiment of the present invention, especially in a process for making a granule, the average residence time of MGDA in step (e) is in the range of from 2 minutes to 4 hours, preferably from 30 minutes to 2 hours.

In another embodiment, especially in a process for making a powder, the average residence time of MGDA in step (e) is in the range of from 1 second to 1 minute, especially 2 to 20 seconds.

In one embodiment of the present invention, the pressure in the drying vessel in step (e) is normal pressure±100 mbar, preferably normal pressure±20 mbar, for example one mbar less than normal pressure.

The solid MGDA formed in step (e) is removed from the spray chamber or spray tower, respectively, in total or in some percentage, continuously or portion-wise.

Together with solid MGDA in the desired particle size, usually smaller particles ("dust" or "fines") and bigger particles ("overs") are formed. The particles with desired size is then separated off from the fines and the overs. Overs may be milled down to an acceptable particle size and returned to the spray chamber or spray tower ("returned"), and fines may be returned as well.

In other embodiments, it is possible to re-dissolve overs and fines in, e.g. water and to reintroduce the solution for spray drying or spray granulation.

It has been found that by performing the inventive process a smaller percentage of overs is formed, and less milling and recycling is required than in case of MGDA with significantly less alkali metal content. On the other hand, the granule obtained by the inventive process has excellent long-term colour stability.

In one embodiment of the present invention, one or more additives may be added to the solution or slurry obtained according to step (d). Examples of useful additives are, for example, titanium dioxide, sugar, silica gel and polymers such as, but not limited polyvinyl alcohol, (co)polymers of (meth)acrylic acid, partially or fully neutralized with alkali. Polyvinyl alcohol in the context of the present invention refers to completely or partially hydrolyzed polyvinyl acetate. In partially hydrolyzed polyvinyl acetate, at least 95 mol-%, preferably at least 96 mol-% of the acetate groups have been hydrolyzed.

In one embodiment of the present invention polyvinyl alcohol used in step (e) has an average molecular weight $M_w$ in the range of from 22,500 to 115,000 g/mol, for example up to 40,000 g/mol.

In another embodiment of the present invention, (co)polymers of (meth)acrylic acid are, for example, random copolymers of acrylic acid and methacrylic acid, random copolymers of acrylic acid and maleic anhydride, ternary random copolymers of acrylic acid, methacrylic acid and maleic anhydride, random or block copolymers of acrylic acid and styrene, random copolymers of acrylic acid and methyl acrylate. More preferred are homopolymers of methacrylic acid. Even more preferred are homopolymers of acrylic acid.

(Co)polymers of (meth)acrylic acid may constitute straight-chain or branched molecules. Branching in this context will be when at least one repeating unit of such (co)polymer is not part of the main chain but forms a branch or part of a branch. Preferably, (co)polymer is not cross-linked.

In one embodiment of the present invention, (co)polymers of (meth)acrylic acid have an average molecular weight $M_w$ in the range of from 1,200 to 30,000 g/mol, preferably from 2,500 to 15,000 g/mol and even more preferably from 3,000 to 10,000 g/mol, determined by gel permeation chromatography (GPC) and referring to the respective free acid.

In one embodiment of the present invention, (co)polymers of (meth)acrylic acid are at least partially neutralized with alkali, for example with lithium or potassium or sodium or combinations of at least two of the forgoing, especially with sodium. For example, in the range of from 10 to 100 mol-% of the carboxyl groups of polymer (B) may be neutralized with alkali, especially with sodium.

In one embodiment of the present invention, (co)polymers of (meth)acrylic acid are selected from per-sodium salts of polyacrylic acid, thus, polyacrylic acid, fully neutralized with sodium.

In one embodiment of the present invention, (co)polymers of (meth)acrylic acid are selected from per-sodium salts of polyacrylic acid with an average molecular weight $M_w$ in the range of from 1,200 to 30,000 g/mol, preferably from 2,500 to 15,000 g/mol and even more preferably from 3,000 to 10,000 g/mol, determined by gel permeation chromatography (GPC) and referring to the respective free acid.

In one embodiment of the present invention the weight ratio of additive to MGDA is in the range of from 1:100 to 1:2, preferably 1:50 to 1:10.

Granules and powders made according to the present invention have excellent with excellent long-term colour stability. They may be generated easily and under economic conditions. The corrosion during manufacture—especially with respect to stainless steel—is excellent.

The invention is further illustrated by working examples.

With exception of ee values, percentages in the context of the examples refer to percent by weight unless expressly indicated otherwise.

I.1. Providing an Aqueous Solution of L-Alanine N,N-Bis Acetonitrile, Step (a.1)

A 5-litre stirred flask was charged with 1,170 g of de-ionized water and heated to 40° C. 668.5 g of L-alanine (99.2 wt-% representing 7.44 mol with >98% ee) were added. To the resultant slurry 390.0 g of 50% by weight aqueous sodium hydroxide solution (4.88 mol) were added over a period of 30 minutes. During the addition the temperature raised to 60° C. After complete addition of the sodium hydroxide the slurry was stirred at 60° C. for 30 minutes. A clear solution was obtained.

At 38 to 42° C. the above solution, formaldehyde as 30% aqueous solution, and HCN (80% of total amount) were added to the first stirred tank reactor in a cascade comprising three stirred tank reactors. In the second stirred reactor additional HCN (20% of total amount) was added at 38-42° C. In the third stirred reactor at 38-42° C., the reaction was completed. An aqueous solution of partially neutralized L-alanine N,N-bis acetonitrile was obtained. It was used as feed for the cold saponification.

I.2 Syntheses of Aqueous Solutions of MGDA-Na$_x$ with Sub-Stoichiometric Amounts or Equimolar Amounts of NaOH: Saponification (b.1)

(b.1-1) Cold Saponification:

The cold saponification was conducted in a cascade of two stirred tank reactors and a tubular reactor. The temperature was approximately 55° C. in all three reactors.

In a first stirred reactor, the feed solution as provided in step (a.1) and NaOH as 50% aqueous solution were added. For completion of the reaction, the mixture was further reacted in a second stirred tank reactor and in a tubular reactor. The solution obtained under steady state conditions was used as feed in the hot saponification.

(b.1-2) Hot Saponification:

The hot saponification was performed at 180° C. and 24 bar in a tubular plug flow reactor at 30 to 45 min retention time. No steps (c) or (d) were performed.

The solution obtained under steady state conditions was expanded to ambient pressure and stirred in a tank reactor at 970 mbar at 94 to 98° C. in order to remove ammonia. Then it was stripped in a wiped film evaporator at 900 mbar at 100° C. to further remove ammonia. Then, the concentration of total complexing agent (A) was adjusted to approximately 40% by weight (based on iron binding capacity).

The molar ratios of the feed materials are summarized in Table 1.

TABLE 1

Summary of comparison examples

| Example | Eq NaOH* | Eq HCN | Eq H$_2$C=O | MGDA-Na$_3$ [wt. %]** | NTA-Na$_3$ [wt. %]*** |
|---|---|---|---|---|---|
| C-1 | 2.86 | 2.03 | 1.98 | 40.27 | 0.05 |
| C-2 | 2.91 | 2.02 | 1.98 | 39.00 | 0.05 |
| C-3 | 2.96 | 2.03 | 1.98 | 40.39 | 0.04 |
| C-4 | 3.00 | 2.03 | 1.98 | 39.11 | 0.07 |

*The equivalents of NaOH refer to the sum of NaOH from the feed solution and NaOH addition during the cold saponification.
**based on iron binding capacity. Expressed as trisodium salt
***based on HPLC Examples according to the present invention:

Steps I.1 and I.2 were performed as above.

I.3 Addition of NaOH

The solution obtained under steady state conditions was submitted in continuous mode to a stirred tank reactor at 970 mbar at 94 to 98° C. An additional amount of NaOH in accordance with Table 2 was added to the stirred tank reactor. Then the combined flows were stripped in a wiped film evaporator at 900 mbar at 100° C. to further evaporate ammonia. Then, the concentration of total complexing agent (A) was adjusted to approximately 40 wt % (based on iron binding capacity).

TABLE 2

Experimental Details

| Example | Eq NaOH* | pH value $^{(x)}$ | Add. EQ of NaOH | Eq HCN | Eq H$_2$C=O | MGDA-Na$_3$ [wt. %]** | NTA-Na$_3$ [wt. %]*** |
|---|---|---|---|---|---|---|---|
| 5 | 2.87 | 9.9 | +0.04 | 2.03 | 1.98 | 39.90 | 0.06 |
| 6 | 2.61 | 9.6 | +0.30 | 2.03 | 1.98 | 40.04 | 0.05 |

*The equivalents of NaOH refer to the sum of NaOH from the feed solution and NaOH addition during the cold saponification.
$^{(x)}$ at the end of respective step (b)
**based on iron binding capacity
***based on HPLC I.4 Addition of NaOH at Ambient Temperature The following examples were prepared corresponding to the aforementioned steps I.1 and I.2, but additional amounts of NaOH were dosed to the product after step I.2 (b.1-2).

A 1-litre stirred flask was charged with 500 g of the corresponding product (after step I.2). Then an additional amount of aqueous sodium hydroxide solution (50 wt.-%) were added at ambient temperature. This solution was heated to 80° C. and stirred for 60 minutes at 80° C. Then the reaction solution was cooled to 20° C. and the concentration of total complexing agent (A) was adjusted to approximately 40 wt % (based on iron binding capacity).

TABLE 3

Experimental Details

| Example | Eq NaOH* | pH value (x) | Add. EQ of NaOH | Eq HCN | Eq H$_2$C=O | MGDA-Na$_3$ [wt. %]** | NTA-Na$_3$ [wt. %]*** |
|---|---|---|---|---|---|---|---|
| 7 | 2.86 | 10.0 | +0.04 | 2.03 | 1.99 | 40.25 | 0.05 |
| 8 | 2.86 | 10.0 | +0.09 | 2.03 | 1.99 | 39.89 | 0.06 |
| 9 | 2.86 | 10.0 | +0.13 | 2.03 | 1.99 | 39.50 | 0.04 |

*The equivalents of NaOH refer to the sum of NaOH from the feed solution and NaOH addition during the cold saponification.
(x) at the end of respective step (b.1-2)
**based on iron binding capacity
***based on HPLC II. Spray Granulation, General Remarks A commercially available laboratory spray granulator with a two-component nozzle and a zigzag air classifier was used, Glatt Lab Systems. The spray granulator was charged with about 1.5 kg of commercially available (Trilon® M) MGDA-Na$_3$. The spray granulator was run according to Table 4. Percentages of overs were determined when the laboratory spray granulator was operated in the steady state.

Then, the solution of MGDA sodium salt was pumped from a stirrer tank to the two-fluid nozzle and then introduced into the laboratory spray granulator. Formation of a granule was observed.

The particles that were large (heavy) enough fell through the zigzag air classifier into a sample bottle, together with value fraction. The sample bottle would contain value fraction and overs. The smaller (lighter) granules were blown through the recycle back into the fluidized bed by the air classifier. Fines were withheld in the granulator with help of the internal filters.

TABLE 4

Parameters of spray granulating

| | C-2.1 Commercially available | C-2.2 Example C-1 | 2.3 Example 9 |
|---|---|---|---|
| Equivalents of NaOH | 3.05 | 2.86 | 2.99 |
| Inlet air temperature [° C.] | 163 to 166 | 163 | 165 |
| Drying air amount [m$^3$/h] | 200 | 200 | 200 |
| Bed temperature [° C.] | 98 to 102 | 97 to 101 | 99 to 100 |
| Nozzle gas pressure [bar] | 4 | 4 | 4 |
| Throughput feed [kg/h] | 6.8 | 7.2 | 7.1 |
| Temperature feed | 25° C. | 70° C. | 70° C. |
| Overs, % by weight referring to contents of sample bottle | 13% | 18% | 5% |

The particles in the sample bottle were classified by a 1000 μm screen. The particles with a diameter of 1000 μm and below constituted the value fraction. The granules over 1000 μm were defined as overs. The overs were milled down with a hammer mill to a diameter of 700 μm maximum and re-introduced into the fluidized bed together with a small share of milled value fraction through the milled product recycle.

In the experiment C-2.1, commercially available MGDA-Na$_3$ solution was used.

The invention claimed is:

1. A process for manufacturing a complexing agent, the process comprising:
   (a) providing a nitrile according to general formula (I a) or (I b):

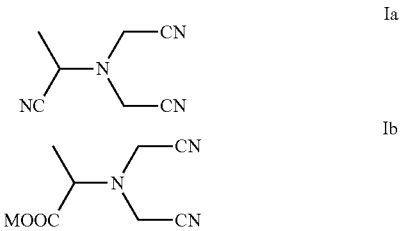

with M being selected from alkali metal and hydrogen and combinations thereof,
   (b) saponifying with a total alkali metal hydroxide amount of 2.5 to 2.9 mol of alkali metal hydroxide per mole of nitrile according to general formula (I a) or (I b), respectively, and a pH value in the range of from 9.5 to 11.5 at the end of step (b),
   (c) adding an amount of alkali metal hydroxide so that the total alkali metal hydroxide content is 2.9 to 3.15 moles per mole of nitrile according to general formula (I a) or (I b), respectively, wherein, if a total of 2.9 moles alkali metal hydroxide per mole of nitrile according to general formula (I a) or (I b) are employed by the end of step (c), the amount of alkali metal hydroxide in the respective step (b) is in the range of from 2.5 to less than 2.9 moles, and
   (d) further saponifying, neutralizing, or removing ammonia.

2. The process according to claim 1, wherein step (d) is neutralizing or saponifying.

3. The process according to claim 1, wherein the nitrile according to formula (I b) is selected from the racemic mixture, enantiomerically pure L-(I b) and mixtures of enantiomers of (I b) in which the L-isomer prevails.

4. The process according to claim 1, wherein the saponification in step (b) is carried out at a temperature in the range of from 25 to 200° C.

5. The process according to claim 1, wherein the alkali metal hydroxide in step (b) or step (c) is potassium hydroxide or sodium hydroxide.

6. The process according to claim 1, wherein the addition of alkali metal hydroxide according to step (c) is performed at a temperature in the range of from 25 to 100° C.

7. The process according to claim 1, wherein in step (c) an amount of alkali metal hydroxide is added so that the total alkali metal hydroxide content is 2.9 to 3.0 moles per mole nitrile according to general formula (I a) or (I b), respectively.

8. The process according to claim 1, further comprising an ammonia removal step between steps (b) and (d).

9. The process according to claim 1, wherein said process comprises the additional step (e) of spray-drying or spray granulating the resultant complexing agent.

* * * * *